(12) United States Patent
Hargrove et al.

(10) Patent No.: US 6,682,751 B1
(45) Date of Patent: *Jan. 27, 2004

(54) CONTROLLED-RELEASE PESTICIDAL COMPOSITION AND METHOD OF MAKING

(75) Inventors: Garrard L. Hargrove, Birmingham, AL (US); John H. Detrick, Gulf Breeze, FL (US)

(73) Assignee: RLC Technologies, L.L.C., Sylacauga, AL (US)

( * ) Notice: Subject to any disclaimer, the term of this patent is extended or adjusted under 35 U.S.C. 154(b) by 77 days.

This patent is subject to a terminal disclaimer.

(21) Appl. No.: 09/949,909

(22) Filed: Sep. 12, 2001

(51) Int. Cl.$^7$ ................................................. A01N 25/32
(52) U.S. Cl. .................. 424/406; 424/407; 424/408; 424/409; 424/417; 424/421; 424/710; 424/514; 424/137; 424/504; 424/101; 424/71; 424/61; 424/64.13
(58) Field of Search ................................ 424/406–410, 424/417, 421, 710; 514/137; 71/61, 64.13; 504/101

(56) References Cited

U.S. PATENT DOCUMENTS

| | | | |
|---|---|---|---|
| 3,716,600 A | * | 2/1973 | Magee ........................ 260/959 |
| 4,056,610 A | | 11/1977 | Barber, Jr. et al. |
| 4,223,070 A | | 9/1980 | Hahn et al. |
| 4,716,659 A | | 1/1988 | Barriquand et al. |
| 4,804,403 A | | 2/1989 | Moore |
| 4,969,947 A | | 11/1990 | Moore |
| 5,073,191 A | * | 12/1991 | Misselbrook et al. .......... 71/121 |
| 5,461,027 A | * | 10/1995 | Bergman ..................... 504/347 |
| 5,939,376 A | | 8/1999 | Durbut et al. |
| 6,013,272 A | * | 1/2000 | Cummings et al. .......... 424/408 |
| 6,060,076 A | | 5/2000 | Voris et al. |
| 6,080,221 A | | 6/2000 | Moore |
| 6,338,746 B1 | * | 1/2002 | Detrick et al. ................. 71/28 |

* cited by examiner

Primary Examiner—Neil S. Levy
(74) Attorney, Agent, or Firm—Breiner & Breiner, L.L.C.

(57) ABSTRACT

A granular controlled-release pesticide comprising "core" granules such as ammonium sulfate, an inner polymer membrane formed in situ on said granules of ammonium sulfate, an acephate pesticide applied to the inner polymer membrane on the core granules, and an outer controlled-release polyurethane membrane formed in situ on said pesticide to permit controlled release of the pesticide.

14 Claims, No Drawings

CONTROLLED-RELEASE PESTICIDAL COMPOSITION AND METHOD OF MAKING

FIELD OF INVENTION

This invention is directed to a composite granular material tailored to release, upon application to soil, plants or the like, a pesticide in a controlled manner. More particularly, the invention is directed to a particulate material comprising a "core" such as ammonium sulfate which is coated under controlled conditions with a select polymeric membrane and a pesticide such as acephate. A controlled-release polymer membrane is applied as an outer membrane. The material is stable when stored, but will release pesticide at a controlled rate when applied to a plant or the like material in a field environment.

BACKGROUND OF THE INVENTION

In recent years, because of ecological concerns as well as the need for controlled release of fertilizers, pesticides and the like materials for economical reasons, there has been a concerted effort to coat fertilizers as well as pesticidal materials with polymer coatings which will permit a controlled release of the material upon application to plants or the like in a field environment.

For example, U.S. Pat. No. 6,060,076 discloses methods and devices for providing long-term protection from intrusion by insects and other cold-blooded animals involving a polymeric matrix and a pesticide contained therein.

Further, U.S. Pat. No. 5,939,376 discloses a controlled-release coated agricultural product including agricultural chemicals, seed, or mixtures thereof with a coating of an environmentally degradable amorphous copolymer. A process of making such products involves making the product with a molten copolymer and then cooling to harden the coating of copolymer upon the agricultural product.

U.S. Pat. No. 4,056,610 discloses a microcapsule insecticide composition including microcapsules, each having a polyurea shell with a photostable ultraviolet light-absorbing compound as an integral part of the shell and a liquid fill capable of slowly permeating the shell of a pyrethroid and a biologically synergist thereof. When the polymer is applied as an insecticide, the pyrethroid releases slowly depending upon the thickness and porosity of the capsule wall.

U.S. Pat. No. 4,223,070 discloses filled porous granules sealed with a porous polyurethane membrane entrapping therein a liquid material. The material is allowed to diffuse from the granules at a controlled rate. The porous granules which are partially miscible with water have applied thereto an organic solution comprising the material to be entrapped, an organic polyisocyanate, and a catalytic amount of a catalyst for catalyzing the polymeric reaction.

U.S. Pat. No. 6,080,221 discloses a method of coating fertilizer particles exhibiting porous surfaces under vacuum to form controlled-release particulate fertilizers by drawing a vacuum on the fertilizer particles and applying thereto a water-insoluble resin at atmospheric pressure and, then hardening the fluid resin to form a solid resin. Pesticides may be coated using the disclosed method.

While these described products are recognized to provide certain improvements with respect to the release of insecticides and the like, the formulations in most respects are difficult to produce, lack essential properties in a controlled-release product or simply can stand improvement.

In a related field it has also been recognized that a fertilizer product, such as urea, can be applied to a soil environment in order to control the release of the fertilizer over a period of time. This permits a single application of the fertilizer which will last several months and possibly an entire growing season, avoiding the need for further applications. For example, U.S. Pat. Nos. 4,716,659; 4,804,403, and 4,969,947, in the name of William P. Moore and now assigned to the assignee of the present application, disclose an attrition-resistant, controlled-release fertilizer comprising a water-soluble central mass, such as urea, containing nucleophilic reaction functional groups surrounding and chemically bonded to a base coating formed by reacting a molecular excess of a coupling agent, such as a polyisocyanate, with the nucleophilic groups of the central mass and a water-insoluble layer surrounding and chemically bonded with the base coating formed by the reaction and polymerization of the excess functional groups of the coupling agent. These products provide outstanding controlled-release fertilizer products.

The present invention is directed to further improved pesticidal materials having controlled-release characteristics when compared with the known materials described in the known prior art.

SUMMARY OF THE INVENTION

In accordance with the present invention, pesticidal products are manufactured having excellent controlled release of the pesticide by bonding the pesticide or a pesticide mixture to a "core" material such as ammonium sulfate using reactive polymer-forming components. Specifically, a core granule has applied thereto an inner polymer membrane. A pesticide or pesticide mixture is applied to the polymer membrane on the core material and bonded thereto, preferably using the reactive components of a polymer matrix. An outer controlled-release polymeric membrane is applied to the inner polymer matrix. The outer controlled-release membrane is formed by using reactive components, such as a polyisocyanate and a polyol such as a polyester. The components of the membrane are controlled so as to permit controlled release of the pesticide and possibly the core granular material when applied to the soil where the product is in contact with moisture.

For convenience, the present invention will be described with reference to an insecticide as the pesticide, and specifically acephate; ammonium sulfate as the granular core material, and a polyurethane as both the inner membrane and the outer controlled-release membrane. It is to be understood, however, that other granular materials such as urea, potassium chloride, clay and the like can be utilized as the core material. Ammonium sulfate is, however, a highly preferred material and provides an excellent pesticidal composition. Further, in addition to using acephate as the pesticide, other pesticides can be utilized, including other insecticides, as well as other components including herbicides, fungicides, plant growth regulators, and the like. The selection of acephate as the pesticide and ammonium sulfate as the granular core material is due to the excellent product formed with these materials and for convenience of description.

DETAILED DESCRIPTION OF THE INVENTION

The present invention will be described with respect to a controlled-release pesticidal material comprising ammonium sulfate as the "core" material, an inner polymer membrane surrounding the core granular material, acephate as the pesticide, and a polyurethane membrane as a controlled-release membrane. In Examples 1 and 2 which follow, these materials are utilized. It is to be understood, however, that modifications can be made in addition to components used with respect to the number of coatings applied to the core material and to the amount of a active component utilized.

EXAMPLE 1

Description of Manufacture of Controlled-Release Acephate Referred to as Type 10 TC (Target Acephate Content=4.3%)

The inner "core" granule is ammonium sulfate. The application of the inner polymer membrane, the bonding procedure and the coating procedure are carried out as follows:

Application of Inner Polymer Membrane and Bonding Procedure (1) 2000 pounds of ammonium sulfate granules (average particle size =1.7 mm) are charged to a rotary drum. The temperature of the granules is kept at 90±10° F.
(2) The rotary drum is turned on and its speed is adjusted to 10 rpm.
(3) 0.43 pounds of polymeric diphenylmethane diisocyanate (p-MDI) (see specifications below) are injected beneath the surface of the rolling bed of ammonium sulfate granules. The p-MDI is allowed to spread over the surface of the granules for one minute.
(4) 2.19 pounds of a polyester polyol/triethanolamine 90%/10% blend (see specifications below) are injected beneath the surface of the rolling bed of ammonium sulfate granules and allowed to spread over the surface of the granules for one minute.

At the conclusion of the above step (4), the p-MDI and polyester polyol/triethanolamine blend have reacted to form the inner polymer membrane.

(5) 9.76 pounds of a fine powder (95% of particles smaller than 0.0029 inch), composed of 1.5% precipitated silica and 98.5% of a commercial pesticide formulation of acephate containing 90% acephate active ingredient, are added to the rolling bed of granules coated with the polyurethane produced in steps (3) and (4). The added powder is allowed to spread over the surface of the coated granules for three minutes.

Acephate active ingredient is O,S-Dimethyl acetylphosphoramidothioate.

(6) 0.67 pounds of p-MDI are injected beneath the rolling bed of granules from step (5), and allowed to spread over the surface of the granules for one minute.
(7) 0.48 pounds of precipitated silica are added to the rolling granules from step (6), and allowed to spread over the surface of the granules for one minute.
(8) Steps (3)–(7) are repeated once, namely
  (a) 0.43 pounds of p-MDI are injected beneath the surface of the rolling bed of granules from Step (7). The p-MDI is allowed to spread over the surface of the granules for one minute.
  (b) 2.19 pounds of a polyester polyol/triethanolamine 90%/10% blend are injected beneath the surface of the granules from step 8(a) and allowed to spread over the surface of the granules for one minute.
  (c) 9.76 pounds of a fine powder (95% of particles smaller than 0.0029 inch), composed of 1.5% precipitated silica and 98.5% of a commercial pesticide formulation of acephate containing 90% acephate active ingredient, added to the rolling bed of granules from step 8(b). The added powder is allowed to spread over the surface of the coated granules for three minutes.
  (d) 0.67 pounds of p-MDI are injected beneath the rolling bed of granules from step 8(d), and allowed to spread over the surface of the granules for one minute.
  (e) 0.48 pounds of precipitated silica are added to the rolling granules from step 8(d), and allowed to spread over the surface of the granules for one minute.
(9) 0.91 pounds of a p-MDI are injected into the rolling bed of granules from step (8). The p-MDI is allowed to spread over the granule surface for one minute.
(10) 4.33 pounds of a polyester polyol/triethanolamine 90%/10% blend are injected beneath the surface of the rolling bed of granules from step (9). The polyol blend is allowed to spread over the surface of the granules for one minute.
(11) 19.52 pounds of the acephate/silica powder blend are added to the rolling bed of granules from step (10), and allowed to spread over the surface of the granules for three minutes.
(12) 1.29 pounds of p-MDI are injected beneath the surface of the rolling granules from step (11). The p-MDI is allowed to spread over the surface of the granules for one minute.
(13) 0.95 pounds of precipitated silica are added to the rolling bed of granules from step (12). The silica is allowed to spread over the surface of the granules for one minute.
(14) Steps (9)–(13) are repeated four more times.

Outer Coating Procedure to Produce 10% Controlled-Release Membrane (1) The granules produced via the above "Inner Polymer Membrane and Bonding Procedure" are heated to 150±10° F. and are maintained at this temperature during the coating procedure.
(2) 2.85 pounds of p-MDI are injected under the surface of the rolling bed of heated rolling granules. The p-MDI is allowed to spread over the surface of the granules for one minute.
(3) 6.42 pounds of a 90%/10% blend of polyester polyol and triethanolamine are injected under the surface of the rolling bed of heated rolling granules. The polyol blend is allowed to spread over the surface of the granules for two minutes.
(4) 4.29 pounds of p-MDI are injected below the surface of the rolling bed of heated rolling granules. The p-MDI is allowed to spread over the surface of the granules for one minute.
(5) Steps (2)–(4) are repeated sixteen (16) more times to produce a total of seventeen (17) polyurethane "layers."
(6) 2.09 pounds of molten wax (see specifications below), a plasticizer for the polyurethane coating, are injected into the hot rolling bed of granules after polyurethane "layers" 3, 6, 9, 12 and 15. Each wax injection is allowed to spread over the surface of the granules for one minute.

| | |
|---|---|
| Theoretical Yield = | 2,403 pounds |
| Actual Yield = | 2,396 pounds |
| | (99.7% of theoretical yield) |
| Outer Coating Target = | 10 weight % |
| Target Acephate Content = | 4.3 weight % |

-continued

| | | |
|---|---|---|
| Product Longevity = (acephate activity) | 4 months @ 20° C. and 2 months @ 30° C. | |

Specifications:

| | | |
|---|---|---|
| (1) p-MDI | NCO content, wt. % | 31–33 |
| | Viscosity @ 25° C., cps | 50–200 |
| | Equivalent wt., grams | 130–133 |
| | Functionality | 2.4–2.8 |
| (2) Polyester polyol | Equivalent wt., grams | 220–250 |
| | Viscosity @ 25° C., cps | 2000–4500 |
| | Functionality | 2 |
| (3) Triethanolamine | triethanolamine, wt %, min | 97.0 |
| | ethanolamine, wt. %, max | 0.5 |
| | diethanolamine, wt. %, max | 3.0 |
| | water, wt. %, max | 0.2 |
| (4) Wax (transitional paraffin) | lbs/gallon | 6.2–6.4 |
| | Viscosity @ 100° C., cSt | 7.1–8.5 |
| | Dropping point, ° F. | 160–168 |
| | Oil content, wt. %, max | 3.0 |
| | Needle penetration @ 77° F., 0.1 mm | 13–15 |

EXAMPLE 2

Description of Manufacture of Controlled-Release Acephate Referred to as Type 18 TC (Target Acephate Content=4.3%)

The inner "core" granule is ammonium sulfate. The application of the inner polymer membrane, the bonding procedure and the coating procedure are carried out as follows:

Application of Inner Polymer Membrane and Bonding Procedure (1) 1,808.44 pounds of ammonium sulfate granules (average particle size=1.7 mm) are charged to a rotary drum. The temperature of the granules is kept at 90±10° F.
(2) The rotary drum is turned on and its speed is adjusted to 10 rpm.
(3) 0.43 pounds of p-MDI are injected beneath the surface of the rolling bed of ammonium sulfate granules. The p-MDI is allowed to spread over the surface of the granules for one minute.
(4) 2.19 pounds of a polyester polyol/triethanolamine 90%/10% blend are injected beneath the surface of the rolling bed of ammonium sulfate granules and allowed to spread over the surface of the granules for one minute.
At the conclusion of step (4), the p-MDI and polyester polyol/triethanolamine blend have reacted to form the inner polymer membrane.
(5) 9.76 pounds of a fine powder (95% of particles a smaller than 0.0029 inch), composed of 1.5% precipitated silica and 98.5% of a commercial pesticide formulation of acephate containing 90% acephate active ingredient, are added to the rolling bed of granules coated with the polyurethane produced in steps (3) and (4). The added powder is allowed to spread over the surface of the coated granules for three minutes.
Acephate active ingredient is O,S-Dimethyl acetylphosphoramidothioate.
(6) 0.67 pounds of p-MDI are injected beneath the rolling bed of granules from step (5), and allowed to spread over the surface of the granules for one minute.
(7) 0.4.8 pounds of precipitated silica are added to the rolling granules from step (6), and allowed to spread over the surface of the granules for one minute.
(8) Steps (3)–(7) are repeated once, namely
 (a) 0.43 pounds of p-MDI are injected beneath the surface of the rolling bed of granules from Step (7). The p-MDI is allowed to spread over the surface of the granules for one minute.
 (b) 2.19 pounds of a polyester polyol/triethanolamine 90%/10% blend are injected beneath the surface of the granules from step 8(a) and allowed to spread over the surface of the granules for one minute.
 (c) 9.76 pounds of a fine powder (95% of particles smaller than 0.002.9 inch), composed of 1.5% precipitated silica and 98.5% of a commercial pesticide formulation of acephate containing 90% acephate active ingredient, are added to the rolling bed of granules from step 8(b). The added powder is allowed to spread over the surface of the coated granules for three minutes.
 (d) 0.67 pounds of p-MDI are injected beneath the rolling bed of granules from step 8(c), and allowed to spread over the surface of the granules for one minute.
 (e) 0.48 pounds of precipitated silica are added to the rolling granules from step 8(d), and allowed to spread over the surface of the granules for one minute.
(9) 0.91 pounds of a p-MDI are injected into the rolling bed of granules from step (8). The p-MDI is allowed to spread over the granule surface for one minute.
(10) 4.33 pounds of a polyester polyol/triethanolamine 90%/10% blend are injected beneath the surface of the rolling bed of granules from step (9). The polyol blend is allowed to spread over the surface of the granules for one minute.
(11) 19.52 pounds of the acephate/silica powder blend are added to the rolling bed of granules from step (10), and allowed to spread over the surface of the granules for three minutes.
(12) 1.29 pounds of p-MDI are injected beneath the surface of the rolling granules from step (11). The p-MDI is allowed to spread over the surface of the granules for one minute.
(13) 0.95 pounds of precipitated silica are added to the rolling bed of granules from step (12). The silica is allowed to spread over the surface of the granules for one minute.
(14) Steps (9)–(13) are repeated four more times.

Outer Coating Procedure to Produce 18% Controlled-Release Membrane (1) The granules produced via the above "Inner Polymer Membrane and Bonding Procedure" are heated to 150±10° F. and are maintained at this temperature during the coating procedure.
(2) 2.64 pounds of p-MDI are injected under the surface of the rolling bed of heated rolling granules. The p-MDI is allowed to spread over the surface of the granules for one minute.
(3) 5.94 pounds of a 90%/10% blend of polyester polyol and triethanolamine are injected below the surface of the rolling bed of heated rolling granules. The polyol is allowed to spread over the surface of the granules for two minutes.
(4) 3.96 pounds of p-MDI are injected under the surface of the rolling bed of heated rolling granules. The p-MDI is allowed to spread over the surface of the granules for one minute.
(5) Steps (2)–(4) are repeated thirty-two (32) times to produce a total of thirty-three (33) polyurethane "layers."

(6) 2.34 pounds of molten wax, a plasticizer for the polyurethane coating, are injected into the hot rolling bed of granules after polyurethane "layers" 3, 7, 11, 15, 19, 23, 27 and 31. Each wax injection is allowed to spread over the surface of the granules for one minute.

| | |
|---|---|
| Theoretical Yield = | 2,403 pounds |
| Actual Yield = | 2,384 pounds |
| | (99.2% of theoretical yield) |
| Outer Coating Target = | 18 weight % |
| Target Acephate Content = | 4.3 weight % |
| Product Longevity = | 8 months @ 20° C. and |
| (Acephate activity) | 4 months @ 30° C. |

It is to be understood with respect to the present invention that the granular "core" material can have various particle sizes. The different particle sizes are chosen in order to meet specific applications as will be known to one skilled in the art.

The effectiveness of the granular pesticides of the present invention are as illustrated in Tables A through G. The pesticides tested are those referred to above in Examples 1 and 2, namely Type 10 TC (Example 1) and Type 18 TC (Example 2). These pesticides were manufactured and tested by Pursell Technologies, Inc. ("PTI"), Sylacauga, Ala. The pesticides were tested in turf. The effectiveness of the pesticides of the invention are compared with Orthene® Tree and Ornamental 75% SP which contains 75% acephate as the active ingredient, except in Table G which also compares the pesticides of the invention with Orthene® Turf, Tree and Ornamental Spray 97 which contains 97% acephate active ingredient; Pinpoint 15 G which contains 15% acephate active ingredient in a granular form, and Battle 9.7 CS which contains Lambda-cyhalothrin, a synthetic pyrethroid. The Orthene product is a sprayable product and was applied to the turf in the tests referred to in Tables A–E upon the detection of the presence of the pests. In some instances, the Orthene spray was applied on more than one occasion as referred to in the Tables A–E. The days after treatment in the Tables A–E refer to days after treatment of the PTI product of Examples 1 and 2. Abbreviations used in the Tables A through G are as follows:

10% TC–4% G=Example 1 Controlled-Release Acephate
18% TC–4% G=Example 2 Controlled-Release Acephate
PTI=Pursell Technologies, Inc. of Sylacauga, Ala.

| | |
|---|---|
| Orthene or Orthene T&O 75% SP = | Orthene ® Tree and Ornamental 75% SP containing 75% acephate active ingredient |
| Orthene TTO 97% S = | Orthene ® Turf, Tree and Ornamental Spray 97 contains, 97% acephate active ingredient |
| Pinpoint 15 G = | Pinpoint ® 15 G which contains 15% acephate active ingredient in granular form |
| Battle 9.7 CS = | Battle Lamba-cyhalotrin which is a synthetic pyrethroid |
| Untreated = | Turf check sample not treated with any pesticide |
| Lbs ai/A = | Pounds of active ingredient applied per acre |
| Lbs Product/A = | Pounds of product applied per acre |
| DAT = | Days after treatment |
| WAT = | Weeks after treatment |

TABLE A

Field Research Data on Acephate Products of Examples 1 and 2
Haiq Point Golf Club - Daufuskie Island, SC
PTI Treatments Applied May 30, 2000
Orthene Sprayable Treatments Applied on June 28 and July 20, 2000

| | | | PERCENT MOLE CRICKET CONTROL | | | | | |
|---|---|---|---|---|---|---|---|---|
| Treatments | Rate Lbs ai/A | Rate Lbs Product/A | 30-May 0 DAT | 21-Jun 22 DAT | 12-Jul 43 DAT | 27-Jul 58 DAT | 14-Aug 76 DAT | 8-Sept 101 DAT |
| 10% TC - 4% G | 4 | 100 | 0 | 93 | 100 | 89 | 81 | 83 |
| 10% TC - 4% G | 8 | 200 | 0 | 100 | 100 | 100 | 98 | 97 |
| 18% TC - 4% G | 4 | 100 | 0 | 96 | 100 | 84 | 81 | 81 |
| 18% TC - 4% G | 8 | 200 | 0 | 97 | 100 | 100 | 98 | 97 |
| Orthene T&O 75% SP | 4 + 4 | NA | — | — | 48 | 54 | 39 | 34 |
| Untreated | 0 | 0 | 0 | 0 | 0 | 0 | 0 | 0 |

TABLE B

Field Research Data on Acephate Products of Examples 1 and 2
Country Club of Hilton Head - Hilton Head Island, SC
PTI Treatments Applied June 6, 2000
Orthene Sprayable Treatments Applied on June 29 and July 21, 2000

| | | | PERCENT IMPORTED FIRE ANT CONTROL | | |
|---|---|---|---|---|---|
| Treatments | Rate Lbs ai/A | Rate Lbs Product/A | 26-Jul 50 DAT | 14-Aug 69 DAT | 7-Sept 93 DAT |
| 10% TC - 4% | 4 | 100 | 93 | 77 | 58 |
| 10% TC - 4% | 8 | 200 | 100 | 85 | 77 |
| 18% TC - 4% | 4 | 100 | 77 | 100 | 87 |
| 18% TC - 4% | 8 | 200 | 100 | 100 | 100 |

TABLE B-continued

Field Research Data on Acephate Products of Examples 1 and 2
Country Club of Hilton Head - Hilton Head Island, SC
PTI Treatments Applied June 6, 2000
Orthene Sprayable Treatments Applied on June 29 and July 21, 2000

| | | | | | |
|---|---|---|---|---|---|
| Orthene T&O 75% SP | 4 + 4 | NA | 27 | 28 | 11 |
| Untreated | 0 | 0 | 0 | 0 | 0 |

| | | | PERCENT MOLE CRICKET CONTROL | | | | |
|---|---|---|---|---|---|---|---|
| Treatments | Rate Lbs ai/A | Rate Lbs Product/A | 6-Jun 0 DAT | 27-Jun 21 DAT | 14-Jul 38 DAT | 26-Jul 50 DAT | 14-Aug 69 DAT | 7-Sept 93 DAT |
| 10% TC - 4% | 4 | 100 | 0 | 78 | 100 | 89 | 85 | 76 |
| 10% TC - 4% | 8 | 200 | 0 | 100 | 100 | 92 | 90 | 79 |
| 18% TC - 4% | 4 | 100 | 0 | 88 | 100 | 76 | 93 | 77 |
| 18% TC - 4% | 8 | 200 | 0 | 100 | 100 | 100 | 99 | 88 |
| Orthene T&O 75% SP | 4 + 4 | NA | — | — | 0 | 68 | 25 | 19 |
| Untreated | 0 | 0 | 0 | 0 | 0 | 0 | 0 | 0 |

TABLE C

Field Research Data on Acephate Products of Examples 1 and 2
St. Simons Island Golf Club - St. Simons Island, GA
PTI Treatments Applied on June 12, 2000 Both Broadcast Surface Versus Subsurface Injected
Orthene Sprayable Applied on June 12 and June 26, 2000.

| | | | PERCENT MOLE CRICKET CONTROL | | | |
|---|---|---|---|---|---|---|
| Treatments | Rate Lbs ai/A | Rate Lbs Product/A | 12-Jun 0 DAT | Surface 26-Jun 2 WAT | Injected 26-Jun 2 WAT | Surface 10-Jul 4 WAT | Injected 10-Jul 4 WAT |
| 10% TC - 4% G | 4 | 100 | 0 | 59 | 87 | 91 | 90 |
| 10% TC - 4% G | 8 | 200 | 0 | 92 | 98 | 93 | 97 |
| 18% TC - 4% G | 4 | 100 | 0 | 82 | 96 | 52 | 89 |
| 18% TC - 4% G | 8 | 200 | 0 | 100 | 100 | 95 | 100 |
| Orthene T&O 75% SP | 4 + 4 | NA | 0 | 13 | 1 | 74 | 61 |
| Untreated | 0 | 0 | 0 | 0 | 0 | 0 | 0 |

| | | | PERCENT MOLE CRICKET CONTROL | | | | | |
|---|---|---|---|---|---|---|---|---|
| Treatments | Rate Lbs ai/A | Rate Lbs Product/A | Surface 24-Jul 6 WAT | Injected 24-Jul 6 WAT | Surface 7-Aug 8 WAT | Injected 7-Aug 8 WAT | Surface 21-Aug 10 WAT | Injected 21-Aug 10 WAT |
| 10% TC - 4% G | 4 | 100 | 92 | 97 | 86 | 98 | 68 | 80 |
| 10% TC - 4% G | 8 | 200 | 100 | 100 | 99 | 100 | 85 | 87 |
| 18% TC - 4% G | 4 | 100 | 84 | 93 | 88 | 91 | 68 | 83 |
| 18% TC - 4% G | 8 | 200 | 100 | 100 | 97 | 100 | 83 | 96 |
| Orthene T&O 75% SP | 4 + 4 | NA | 85 | 71 | 55 | 53 | 47 | 47 |
| Untreated | 0 | 0 | 0 | 0 | 0 | 0 | 0 | 0 |

TABLE D

Field Research Data on Acephate Products of Examples 1 and 2
St. Simons Island Golf Club - St. Simons Island, GA
PTI Treatments Applied on June 26, 2000
Orthene Sprayable Treatments Applied On June 26 and July 10, 2000

| | | | PERCENT MOLE CRICKET CONTROL | | | | |
|---|---|---|---|---|---|---|---|
| Treatments | Rate Lbs ai/A | Rate Lbs Product/A | 26-Jun 0 WAT | 10-Jul 2 WAT | 24-Jul 4 WAT | 7-Aug 6 WAT | 21-Aug 8 WAT |
| 10% TC - 4% C | 4 | 100 | 0 | 50 | 93 | 84 | 75 |
| 10% TC - 4% G | 8 | 200 | 0 | 62 | 99 | 96 | 88 |
| 18% TC - 4% G | 4 | 100 | 0 | 69 | 92 | 83 | 73 |
| 18% TC - 4% G | 8 | 200 | 0 | 83 | 100 | 98 | 86 |
| Orthene T&O 75% SP | 4 + 4 | NA | 0 | 94 | 95 | 67 | 31 |
| Untreated | 0 | 0 | 0 | 0 | 0 | 0 | 0 |

TABLE E

Field Research Data on Acephate Products of Examples 1 and 2
University of Florida - Milton, FL
PTI Treatments Applied on Jul. 18, 2000
Orthene Sprayable Treatments Applied on
Aug. 10 and Sep. 1, 2000

| Treatments | Rate Lbs ai/A | Rate Lbs Product/A | PERCENT MOLE CRICKET CONTROL | | | |
|---|---|---|---|---|---|---|
| | | | 18-Jul 0 DAT | 3-Aug 2 WAT | 25-Aug 5 WAT | 12-Sept 8 WAT |
| 10% TC-4% G | 4 | 100 | 0 | 0 | 50 | 64 |
| 10% TC-4% G | 8 | 200 | 0 | 47 | 79 | 72 |
| 18% TC-4% G | 4 | 100 | 0 | 0 | 61 | 76 |
| 18% TC-4% G | 8 | 200 | 0 | 12 | 72 | 81 |
| Orthene T&O 75% SP | 4 + 4 | NA | 0 | 0 | 26 | 55 |
| Untreated | 0 | 0 | 0 | 0 | 0 | 0 |

TABLE F

Field Research Data on Acephate Products of Examples 1 and 2
Imported Red Fire Ant Control at USDA, APHIS
Plant Protection Station, Gulfport, MS
PTI treatments applied on Aug. 10, 2000

| Treatments | Rate Lbs ai/A | Rate Lbs Product/A | PERCENT IMPORTED FIRE ANT CONTROL % Decrease in Number of Colonies | |
|---|---|---|---|---|
| | | | Test 1 6 WAT | Test 2 6 WAT |
| 10% TC-4% G | 4 | 100 | 57 | 59 |
| 10% TC-4% G | 8 | 200 | 77 | 87 |
| 18% TC-4% G | 4 | 100 | 60 | 63 |
| 18% TC-4% G | 8 | 200 | 78 | 85 |
| Untreated | 0 | 0 | 43 | 47 |

TABLE G

Field Research Data on Acephate Products of Examples 1 and 2
Late Season Adult Mole Cricket Control - Savannah, Georgia
All Treatments Applied on September 28, 2000
Mole crickets = 5th Stage Adult at Application Time

| Product | Lbs ai/A | PRE | PERCENT MOLE CRICKET CONTROL | | | | | | |
|---|---|---|---|---|---|---|---|---|---|
| | | | 1 WAT | 2 WAT | 3 WAT | 4 WAT | 8 WAT | 12 WAT | 16 WAT |
| Orthene TTO 97% s | 3.88 | 4 | 65 | 93 | 77 | 49 | 49 | 39 | 41 |
| Pinpoint 15 G | 4.05 | 9 | 81 | 100 | 82 | 89 | 60 | 59 | 51 |
| Battle 9.7 CS | 0.1375 | 0 | 76 | 99 | 90 | 90 | 72 | 67 | 56 |
| 10% TC - 4% G | 3 | 0 | 58 | 100 | 81 | 80 | 55 | 75 | 68 |
| 10% TC - 4% G | 4 | 0 | 57 | 99 | 90 | 92 | 88 | 100 | 92 |
| 10% TC - 4% G | 5 | 0 | 72 | 100 | 95 | 98 | 97 | 100 | 100 |
| Untreated Check | | | 0 | 0 | 0 | 0 | 0 | 0 | 0 |

Table A compares the effectiveness of Examples 1 and 2 to commercial product, i.e., Orthene Tree and Ornamental 75% SP, with respect to mole cricket control in turf. Also shown are the results where no treatment is made. The tests were carried out by surface application to turf at Haig Point Golf Club, Daufuskie Island, S.C. As will be apparent, the products of the present invention are greatly superior to either the use of Orthene Tree and Ornamental or no treatment.

Table B similarly compares the imported fire ant control and the mole cricket control of Examples 1 and 2 of this invention to that achieved with Orthene Tree and Ornamental 75% SP. Also shown are the results where no treatment is made. The tests were carried out by surface application at Country Club of Hilton Head, Hilton Head Island, S.C.

Table C is similar to Table B, but includes a different method of application. Specifically the products of Examples 1 and 2 were applied both by the broadcast method over the surface and were applied by injection into the subsurface. However, the advantages and effectiveness of the pesticides of the present invention are readily apparent. The tests were carried out at St. Simons Island Golf Club, St. Simons Island, Ga.

Table D is similar to Tables A and B, and records tests carried out at St. Simons Island Golf Club, St. Simons Island, Ga., and again shows the effectiveness of the pesticides of the present invention over commercial products.

Table E reporting tests carried out at the University of Florida, Milton, Fla., again establishes the effectiveness of the pesticides of the present invention versus commercial products for mole cricket control.

Table F establishes the effectiveness of the products of the present invention for the control of imported red fire ants conducted at the Plant Protection Station, Gulfport, Miss.

Table G establishes the effectiveness of the products of the invention for late season adult mole cricket control. The advantages of the claimed invention over commercial products are established.

It will be understood by those skilled in the art that the granular core material can have various particle sizes, with the different particle sizes being chosen in order to meet specific applications as will be known to one skilled in the art. Further, the number of coatings applied will determine the amount of pesticide applied. The amount of pesticide applied will vary according to the needs of a particular application.

As will be apparent to one skilled in the art, various modifications can be made within the scope of the aforesaid description. Such modifications being within the ability of one skilled in the art form a part of the present invention and are embraced by the appended claims.

What is claimed is:

1. A granular pesticide comprising a core material coated with an inner polymer membrane formed in situ on the core material, a pesticide applied to the inner polymer membrane on the core material, and an outer controlled release polymer membrane formed in situ on the pesticide to permit controlled release of the pesticide.

2. The granular pesticide of claim 1 wherein the core material is ammonium sulfate.

3. The granular pesticide of claims 1 or 2 wherein the pesticide is acephate.

4. The granular pesticide of claims 1 or 2 wherein the inner polymer membrane is formed in situ from a diisocyanate and a polyol.

5. The granular pesticide of claim 4 wherein the diisocyanate is polymeric diphenylmethane diisocyanate.

6. The granular pesticide of claim 4 wherein the polyol is a polyester polyol.

7. The granular pesticide of claim 6 wherein the polyester polyol is blended with triethanolamine.

8. The granular pesticide of claims 1 or 2 wherein the outer controlled release polymer membrane is formed in situ from a diisocyanate and a polyol.

9. The granular pesticide of claim 8 wherein the diisocyanate is polymeric diphenylmethane diisocyanate.

10. The granular pesticide of claim 8 wherein the polyol is a polyester polyol.

11. The granular pesticide of claim 10 wherein the polyester polyol is blended with triethanolamine.

12. The granular pesticide of claim 7 wherein said granular pesticide is coated with a plurality of layers of pesticide.

13. The granular pesticide of claim 3 wherein the inner polymer membrane is formed in situ from a diisocyanate and a polyol.

14. The granular pesticide of claim 3 wherein the outer controlled release polymer membrane is formed in situ from a diisocyanate and a polyol.

* * * * *

UNITED STATES PATENT AND TRADEMARK OFFICE
CERTIFICATE OF CORRECTION

PATENT NO. : 6,682,751 B1
DATED : January 27, 2004
INVENTOR(S) : Garrard L. Hargrove and John H. Detrick It is certified that error appears in the above-identified patent and that said Letters Patent is hereby corrected as shown below:

Column 1,
Line 60, "and, then" should read -- and then --.
Line 67, "product or" should read -- product, or --.

Column 3,
Line 7, "a active" should read -- active --.

Column 4,
Line 7, "step 8(d)" should read -- step 8(c) --.

Column 5,
Line 55, "a smaller" should read -- smaller --.

Column 8,
Table A, line 2 of heading, "Haiq Point Golf Club" should read -- Haig Point Golf Club --.

Signed and Sealed this

Twenty-seventh Day of April, 2004

JON W. DUDAS
*Acting Director of the United States Patent and Trademark Office*